United States Patent [19]

Aldrett

[11] Patent Number: 5,163,931
[45] Date of Patent: Nov. 17, 1992

[54] SUBSTANTIALLY HYDROPHOBIC AND BIODEGRADABLE LAMINAR CELLULOSE MATERIAL, ITS MANUFACTURING METHOD, AND SUBSTANTIALLY BIODEGRADABLE DISPOSABLE DIAPERS MADE OF SAID MATERIAL

[76] Inventor: Pablo Aldrett, Homero 1433, Mexico, D.F., Mexico, 11560

[21] Appl. No.: 636,719

[22] Filed: Jan. 2, 1991

[51] Int. Cl.$^5$ ............ A61F 13/15; A61F 13/20; D21F 11/00; D21H 23/00
[52] U.S. Cl. .................... 604/374; 604/358; 604/375; 162/158
[58] Field of Search ............ 106/210, 287.25; 162/158, 175; 604/358, 374, 375

[56] References Cited

U.S. PATENT DOCUMENTS

| | | | |
|---|---|---|---|
| 3,887,427 | 6/1975 | Helmer et al. | 162/158 |
| 3,931,069 | 1/1976 | Lundin | 162/158 X |
| 3,990,939 | 11/1976 | Aldrich et al. | 162/158 X |
| 4,207,142 | 6/1980 | Shepherd | 162/158 |
| 4,214,948 | 7/1980 | Mazzarella et al. | 162/158 |
| 4,240,935 | 12/1980 | Dumas | 162/158 X |
| 4,243,481 | 1/1981 | Dumas | 162/158 |
| 4,295,931 | 10/1981 | Dumas | 162/158 |
| 4,317,756 | 3/1982 | Dumas | 162/158 X |
| 4,964,915 | 10/1990 | Blixt et al. | 106/210 |

OTHER PUBLICATIONS

Hercules, Inc. on Benefits of Using Aquapel.
Sizing with Alkylketene Dimers, W. O. Kincannon Jr. and S. H. Watkins, Special Sizes.

*Primary Examiner*—David Isabella
*Assistant Examiner*—Elizabeth M. Burke
*Attorney, Agent, or Firm*—Jacobson, Price, Holman & Stern

[57] ABSTRACT

A substantially hydrophobic and biodegradable laminar cellulose-base material consisting of a cellulose-base woven fabric treated with a reaction agent emulsified with a cationic starch and water together with a retention agent is disclosed. Novel assemblies of disposable goods useful for collecting corporal fluids excreted by human body are also disclosed.

3 Claims, No Drawings

SUBSTANTIALLY HYDROPHOBIC AND BIODEGRADABLE LAMINAR CELLULOSE MATERIAL, ITS MANUFACTURING METHOD, AND SUBSTANTIALLY BIODEGRADABLE DISPOSABLE DIAPERS MADE OF SAID MATERIAL

BACKGROUND OF THE INVENTION

1. Field of the Invention

The present invention relates to a cellulose material which has hydrophobic and biodegradable properties.

2. Prior Art

The there are two basic techniques for the waterproofing of textiles: the first involves the sealing of the pores of the said textile material. The second is achieved by applying a film of a plastic material on top of the textile material.

Plastic linings are applied by means of various techniques, such as: 1) application of the plastic material to the textile material, subsequent passage under a blade to remove the excess lining, baking the material in a hot oven and then running it through an ironing machine (calender) to press the lining inside the textile material; 2) submerge the textile material in the plastic product; 3) press a plastic film against a textile material; and 4) soften or melt the plastic by applying heat, such that a the former is bound permanently to the textile material.

Waterproofing by closing the pores of textile materials is commonly achieved by treatment with insoluble metal compounds such as aluminum soap, basic aluminum acetate, cuprammonium, paraffin or mixtures of waxes, bituminous materials such as asphalt or tar, and linseed oil or other drying oils.

In terms of the physical phenomenon involved in the waterproofing of textile materials by narrowing the pores of the fibers, it can be said that the waterproofing obtained results in a hydrophobic condition characterized by a degree of water repellency or rejection, in the sense that it prevents the penetration of in water.

The intended use of the textile material determines whether the material must be waterproof, water repellent, resistant to spots, etc. The disposable diaper is one of the many items that require a textile material which is practically waterproof, while preserving its original characteristic properties such as lightness, ease of handling and, above all, biodegradability, the material being a natural fiber such as cotton, for example.

At this time, no textile material with all the properties described above is available for practical applications. Accordingly, practically the disposable diapers available right now, made a of waterproofed textile materials, are based on the use of layers or sheets of plastic materials, primarily polyethylene mixed with plastic additives, which acts as the external lining which carries and contains the entire disposable diaper.

In recent years, this has raised serious environmental problems because the diaper and its contents was enclosed in a sheet of non-degradable plastic which did not allow the degradation of the contents by the bacteria and microorganisms found in the environment, to the effect that the diaper and its content can remain practically intact for many years.

The situation is further exacerbated by the worldwide increase in the use of this particular type of diapers. According to USA estimates, 85-90% of the North American infants use disposable diapers, the average consumption from birth to the completion of toilet training being equal to 7,800 diapers per infant. According to these figures, the North American babies alone account for the use of 15.8 to 18 billion disposable diapers per year. These figures are even higher when one considers the incontinent adults who also use disposable diapers.

The present invention solves the above mentioned problems with a novel material that is both biodegradable and compatible with the manufacturing of a diaper which has biodegradable contents.

Further, the present invention is directed to a new method for the production of a hydrophobic cellulose material, preferably made of cotton fibers, which can be used satisfactorily to manufacture disposable diapers that are substantially biodegradable, among others.

SUMMARY OF THE INVENTION

The object of the present invention is a method according to which a cellulose material, preferably cotton fibers, is treated with a combination of alkyl ketene, modified cornstarch and a cationic retention agent, to obtain a cellulose material which is substantially both hydrophobic and biodegradable. The materials prepared according to the method and the disposable diapers manufactured of the materials are also claimed by the present invention. The treatment of the said cellulose material involves a chemical reaction between the alkyl ketene dimer and the cellulose, in the presence of a fiber of suitable quality, the completion of the reaction results in the formation of bridges which account for the narrowing of the pores of the cotton fiber, such that the passage of water across the fiber is greatly delayed and, as a result, the fiber becomes substantially hydrophobic or waterproof.

In addition, the presence of a cationic retention agent during the chemical reaction agent promotes both the contact and the reaction between the dimer particles and the cellulose.

Since the alkyl ketene dimer, the cationic starch and the cationic retention agent are substantially biodegradable, it follows that the cellulose material obtained fully preserves its biodegradability.

Accordingly, one object of the present invention is a cellulose material, preferably made of cotton fibers, which substantially hydrophobic and substantially biodegradable.

Another object of the invention is to obtain a cellulose material, preferably made of cotton fibers, which when used with an adequate woof, is substantially impermeable to aqueous liquids, as well as biodegradable. Another object of the invention is a method for the preparation of a cellulose material, preferably made of cotton fibers, substantially hydrophobic and substantially biodegradable.

Still another object of the invention is the production of disposable diapers made of a cellulose material, preferably cotton fibers, which are substantially hydrophobic and highly biodegradable.

Another object of the invention is a method for the manufacturing of disposable diapers made of cellulose material, preferably cotton fibers, which are highly biodegradable.

These and other objects of the invention will be better understood from the following detailed description:

BRIEF DESCRIPTION OF THE INVENTION

A substantially hydrophobic and biodegradable laminar cellulose material which is provided with a layer of basic cellulose material treated with an alkyl ketene dimer emulsified with a cationic starch and water, as well as a retention agent.

The cellulose material is produced by a method, consisting of the steps of:

a) preparing a bath having an emulsion of alkyl ketene dimer in cationic starch and water, and a retention agent, wherein the water has an alkaline pH;
b) saturating a basic laminar cellulose material with the products used in step a);
c) heat-drying the saturated laminar cellulose material and accelerating the reaction between the alkyl ketene dimer and cellulose; and
d) terminating the chemical reaction.

DETAILED DESCRIPTION OF THE INVENTION

According to the present invention, a cellulose material, preferably cotton fibers, undergoes a treatment which consists of the following basic stages:
a) preparation of the emulsion;
b) saturation of the cellulose material and start of the reaction;
c) drying and acceleration of the reaction;
d) end of the chemical reaction.

a) The preparation of the emulsion is carried out in a vessel containing water at a temperature ranging from 63° to 90° C., which is fed modified corn starch at the rate of about 2.5% to 4.5% by weight, followed by the addition of alkyl ketene dimer in an amount calculated such that the final emulsion contains about 3-12%, by weight, of the said dimer. After the addition of these two components, emulsification is performed in an emulsifying setup at a pressure of about 3,000 psi.

Separately, an aqueous solution of the cationic retention agent is prepared. The said agent is selected from a group consisting of Kymene 557, Reten 763, Reten 205 MX and cationic starch (Kymene and Reten are registered trademarks of Hercules Inc.).

According to the "Dictionary of Chemistry and Chemical Products", Gessner G. Hawley, Ed. Omega. 1988 Reprinting, pages 506 and 742: Kymene consists of polyamide-epichlorhydrin cationic resins; Reten 205 is a water-soluble synthetic polymer of high molecular weight and strongly cationic; Reten 763 is an aqueous solution of a modified polyamide-epichlorhydrin resin. Reten is used as flocculating, agglutinating and viscosity regulating agent.

The approximate concentrations of these agents in the solutions claimed by the present invention are:

| | |
|---|---|
| Kymene 557 | 0.05% to 0.20% |
| Reten 763 | 0.05% to 0.20% |
| Reten 205 MX | 0.05% to 0.10% |
| Cationic starch | 0.03% to 2.00% | b) A vessel containing water at a temperature of about 40°-50° C., with a slightly alkaline pH (pH=7-8) by adding a regulating agent with a base of base of sodium carbonate, is used to prepare a bath with the processing substances, by adding the emulsion described above and the cationic retention agent.

The textile material is submerged in water for a certain period of time, preferably 1 to 3 minutes, such that the said textile material becomes saturated with the solution of dimer-starch-retention agent-water.

It is though that the contact between alkyl ketene dimer and the hydroxyl radical of cellulose results in the formation of the $\beta$-keto ester. The rate of this reaction increases according to the increase in temperature and pH; moreover, it was established that the reaction continues even after the drying process.

c) The textile material, saturated with the materials mentioned earlier, is transferred to a drying conveyor to remove the water and also to accelerate the rate of the reaction. Drying is carried out at a temperature range of about 65° to 160° C., for a period of 2 to 5 minutes.

d) In order for the reaction to reach the point where the material presents hydrophobic properties, approximately 80% through the reaction, the laminar cellulose material obtained must be rested for at least 24 hours. In actual practice, is was established that the reaction is completed in a period of approximately two weeks.

When using a cellulose with an adequate woof, 72 $g/m^2$, for example, the material obtained after 24 hours of drying presents substantial waterproofing properties.

At the end of a time period ranging from 24 hours to 2 weeks following the completion of the drying process, the cellulose material obtained was substantially hydrophobic (or waterproof, depending on the woof used) and biodegradable.

A preferred, non-limiting embodiment of the present invention is described below. It is understood that the said example by no means limits or restricts the coverage of the invention to the examples and methods described, which are given only for illustrative purposes.

EXAMPLE

An emulsion is prepared by dispersing the alkyl ketene dimer in a cationic starch/water solution having a concentration ranging from 2.5 to 4.5% by weight, at a temperature of 70° C. Emulsification is carried out under a high pressure emulsification setup at a pressure of 3000 psi.

To the vessel with water at 45° C. was added a solution of sodium bicarbonate to achieve a pH of about 7.6. To the emulsion was then added a retention agent, Kymene 557 (trademark of Hercules Inc.) in a concentration equivalent to approximately 4.0 grams of agent per kilogram of textile material being processed.

Single samples of a textile material made of cotton fibers and having a woof of 72 $g/m^2$ are first submerged in the above bath, for various periods of time, as indicated in the table presented below, and then dried at a temperature ranging from 65° to 160° C.

The cellulose materials obtained are then tested to determine the time in which a drop of water is absorbed by the cellulose material prepared as described above, in normal conditions of pressure and temperature. The tests involves the dropping of a drop of water on the horizontally suspended cellulose material. The absorption time recorded in each case is expressed in terms of the time lapsed before the start of the deformation of the drop, which means that, during the said time, the drop is not completely absorbed by the material claimed by the present invention.

The results obtained are presented in the following Table.

| Soaking time of the material in the processing solution | Absorption time of the drop in the cellulose material prepared |
|---|---|
| 0 seconds | 6 seconds |
| 15 seconds | 1 hour |
| 60 seconds | 6 hours |
| 120 seconds | 6.3 hours |
| 180 seconds | 7.5 hours |

The results of the tests demonstrate that the cellulose material claimed by the present invention has significant waterproofing characteristics to aqueous liquids.

Manufacturing of disposable diapers

Using conventional manufacturing techniques, the material claimed by the present invention can be used to produce disposable diapers, as described below:

a) Bleached, ground wood cellulose is used to prepare tissue paper, forming a cushion of a suitable shape;

b) The lower portion of the cellulose cushion is placed on a suitable piece of laminar cellulose material of a suitable woof, which was first waterproofed according to the treatment claimed by the present invention.

c) After preparing the cushion with the piece of the material claimed by the invention at its bottom, the upper portion of the said cushion is also lined with a second layer of laminar cellulose material prepared according to the invention, except that woof of the textile fibers used in this case is lower (i.e. fewer transversal yarns per unit of surface, equivalent to approximately 46 g/m$^2$, for example).

d) The tightening means used to fasten and adjust the diaper to the infant are added next.

e) The sealing, folding and cutting of the diaper are also performed during this assembly operation. Sealing is achieved by placing longitudinal lines of an adhesive which seals the edges and the transversal ends of the diaper.

The current processes for the manufacturing of disposable diapers use a film or sheet made of plastic, as a general rule a polymer mixed with other additives. As well known, polyethylene is practically non-biodegradable. However, according to the method for the manufacturing of disposable diapers claimed by the present invention, the plastic sheet is replaced by a special layer of cellulose material prepared according to the invention, which is hydrophobic and, because of its woof (which is equivalent to a weight of approximately 70 g/m$^2$, for example), is substantially waterproof and biodegradable.

The current processes for the manufacturing of disposable diapers, as a general rule use a film of a permeable material, usually polypropylene, which is also non-biodegradable, to channel the flow of aqueous liquid to the cellulose layer and also to prevent the contact between the liquids and the skin of the infant. However, according to the process for the manufacturing of disposable diapers claimed by the present invention, the polypropylene film is replaced by a sheet of the cellulose material claimed by the invention, except that in this case the material is preferably made of cotton fibers, with a lower woof or fewer threads per unit of surface (equivalent to a weight about 50 g/m$^2$, for example). This sheet of material, which is also biodegradable and channels the flow of liquid to the cellulose cushion, was also prepared according to the process claimed by the present invention and, by being substantially hydrophobic, does not allow the liquids to come in contact with the skin of the infant, since the liquids are absorbed by the cellulose cushion.

The methods and the products obtained with the methods, were described only for a better understanding of the invention, being understood that many changes can be made without exceeding the scope of the invention, the changes being covered by the invention which is limited only by the claims defined below.

I claim:

1. A substantially hydrophobic and substantially biodegradable cloth consisting of
a sheet of a cellulose-base woven fabric comprised of fibers creating a weft and a warp said fibers selected from the group consisting of cotton and flax fibers, wherein said fabric is made substantially hydrophobic by treating said fabric with a dimer of an alkyl ketene emulsified with a cationic starch and water to impart a narrowing of interslices between said fibers.

2. The cloth of claim 1 wherein the cellulose-base fabric is a fabric with a high woof.

3. The cloth of claim 1, wherein the cellulose-base fabric is a fabric with a low woof.

* * * * *